United States Patent [19]

Parker

[11] Patent Number: 5,769,830
[45] Date of Patent: Jun. 23, 1998

[54] SOFT TIP GUIDING CATHETER

[75] Inventor: Fred T. Parker, Bloomington, Ind.

[73] Assignee: Cook Incorporated, Bloomington, Ind.

[21] Appl. No.: 299,773

[22] Filed: Sep. 1, 1994

Related U.S. Application Data

[63] Continuation-in-part of Ser. No. 80,697, Jun. 22, 1993, abandoned, which is a continuation of Ser. No. 725,754, Jun. 28, 1991, Pat. No. 5,221,270.

[51] Int. Cl.$^6$ ................................................ A61M 25/00
[52] U.S. Cl. .......................... 604/282; 604/280; 604/264; 138/124; 138/138
[58] Field of Search .................................. 604/280, 281, 604/282, 264, 103, 95, 96; 128/656–658; 138/118, 124, 138, 125, 123, 132, 137, 140, 143, 144, 133, 134

[56] References Cited

U.S. PATENT DOCUMENTS

| | | |
|---|---|---|
| 3,529,633 | 9/1970 | Vaillancourt . |
| 4,385,635 | 5/1983 | Ruiz ........................................ 128/658 |
| 4,563,181 | 1/1986 | Wijayarathna et al. ................ 604/280 |
| 4,636,346 | 1/1987 | Gold et al. . |
| 4,735,620 | 4/1988 | Ruiz ........................................ 604/281 |
| 4,863,442 | 9/1989 | DeMello et al. ........................ 604/282 |
| 4,886,506 | 12/1989 | Lovgren et al. ........................ 604/282 |
| 4,898,591 | 2/1990 | Jang et al. . |
| 4,913,701 | 4/1990 | Tower ..................................... 606/192 |
| 5,017,259 | 5/1991 | Kohsai . |
| 5,078,702 | 1/1992 | Pomeranz . |
| 5,085,649 | 2/1992 | Flynn ...................................... 604/282 |
| 5,254,107 | 10/1993 | Soltesz ..................................... 604/282 |
| 5,279,596 | 1/1994 | Castaneda et al. ..................... 604/282 |
| 5,403,292 | 4/1995 | Ju .............................................. 604/264 |

FOREIGN PATENT DOCUMENTS

| | | |
|---|---|---|
| 0273618 | 7/1988 | European Pat. Off. . |
| 0303487 | 2/1989 | European Pat. Off. . |

*Primary Examiner*—Ronald K. Stright, Jr.
*Attorney, Agent, or Firm*—Richard J. Godlewski

[57] ABSTRACT

A soft tip guiding catheter for atraumatic insertion into delicate, tortuous coronary vessels and introduction of an angioplasty balloon catheter therethrough. The guiding catheter includes a main tubular portion and a soft tubular tip with cooperating bonding surfaces for increasing the contact area and strength of the thermal bond therebetween. The cooperating bonding surfaces each include a proximal ground taper portion with a braid material included therein and a distal longitudinal portion without the braiding material. The main portion preferably includes an inner layer of lubricous material, an outer layer of a polyether block amide, and a reinforcing braid positioned therebetween. The main tubular portion also includes distal and proximal segments heat shrink bonded together to provide changes in durometer along the length of the catheter. The layers of the main portion provide a thin catheter wall with pushability, torquability, and kink resistance.

19 Claims, 2 Drawing Sheets

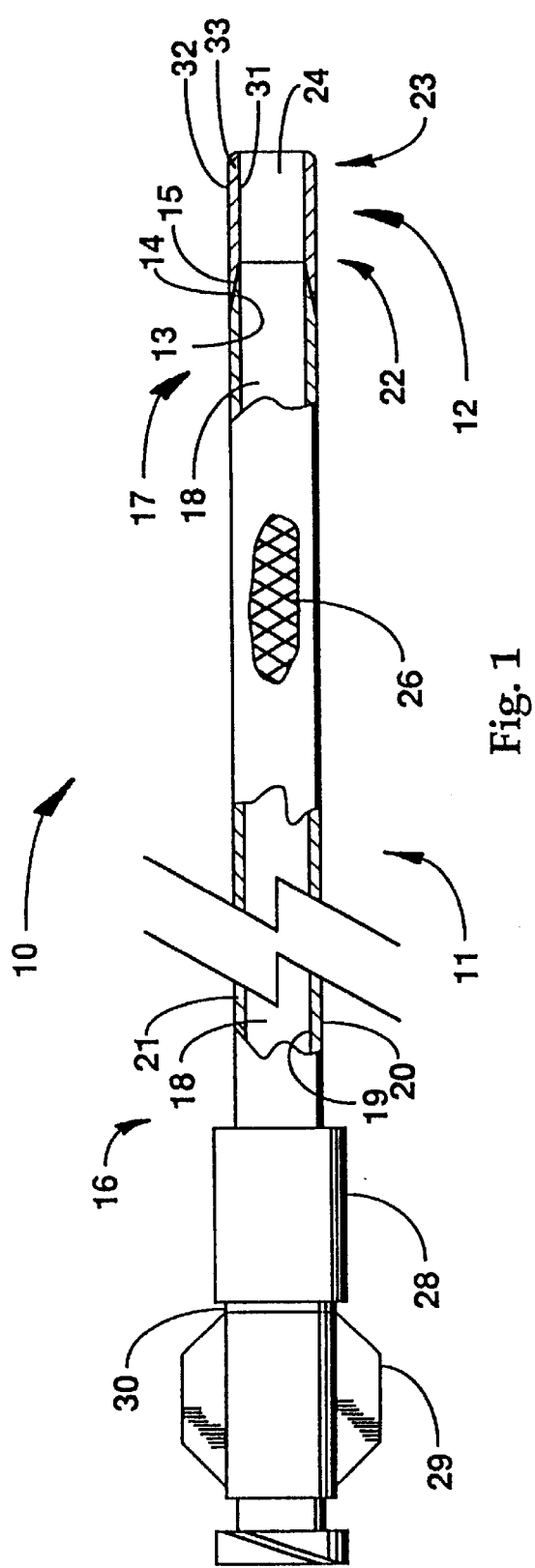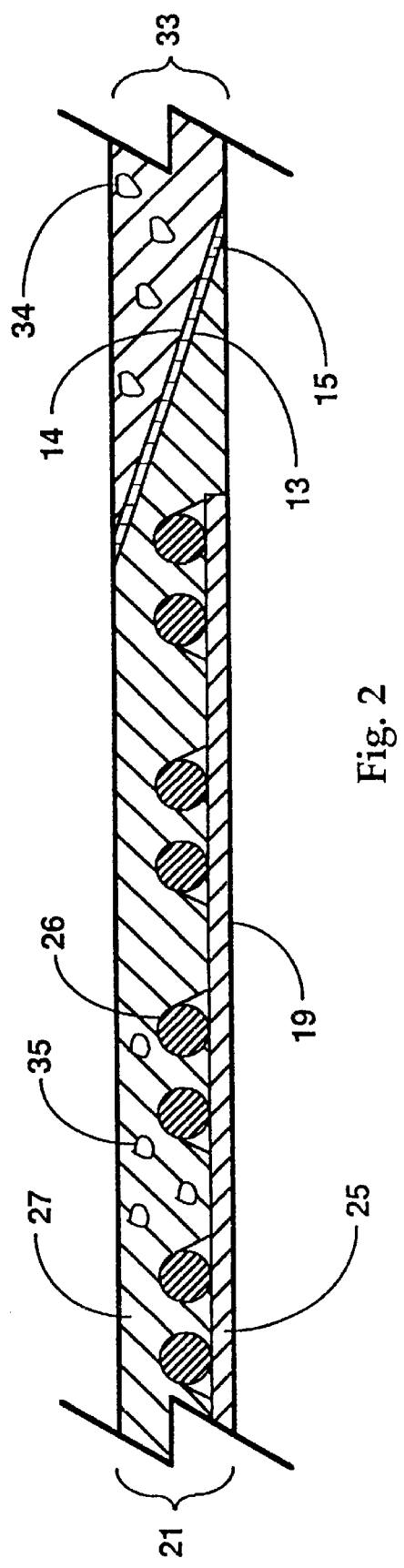

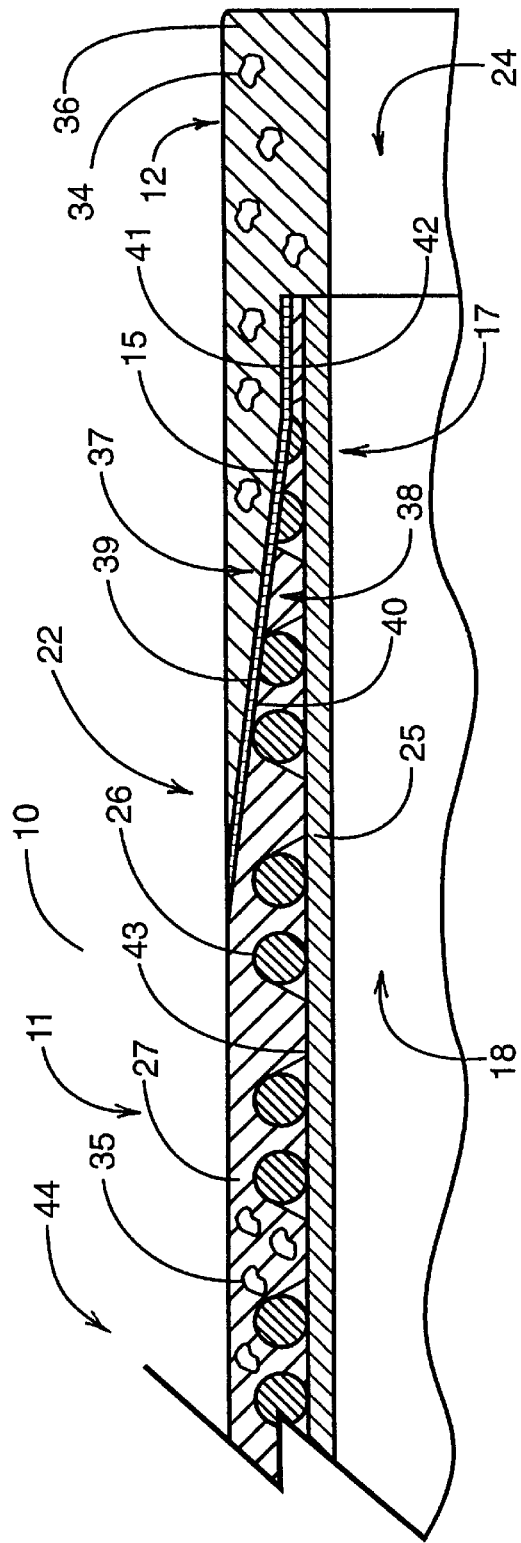
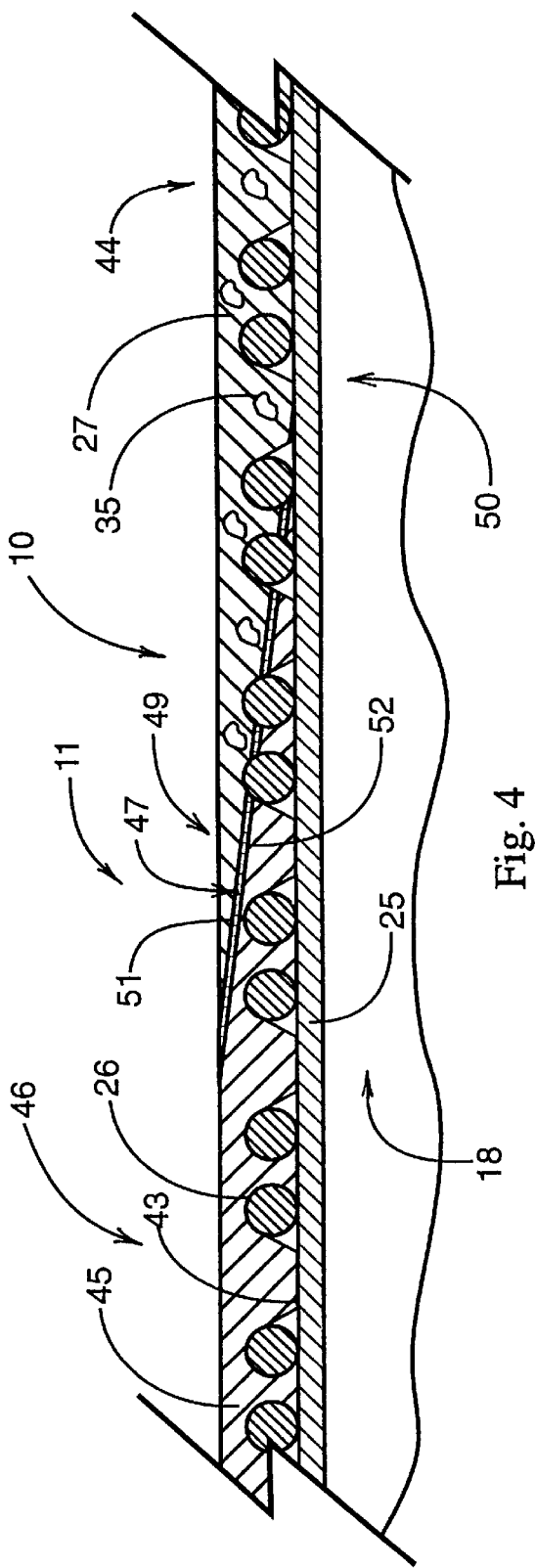
Fig. 3
Fig. 4

SOFT TIP GUIDING CATHETER

CROSS-REFERENCE TO RELATED APPLICATIONS

This application is a continuation-in-part of application Ser. No. 08/080,697, filed Jun. 22, 1993, now abandoned which is a continuation of application Ser. No. 07/725,754, filed Jun. 28, 1991, now U.S. Pat. No. 5,221,270, both applications being entitled "Soft Tip Guiding Catheter".

TECHNICAL FIELD

This invention relates generally to guiding catheters and, in particular, to a guiding catheter with a soft distal tip.

BACKGROUND OF THE INVENTION

Guiding catheters are commonly used during coronary angioplasty procedures for delivering a balloon catheter to a treatment site in a coronary vessel. To move a guiding catheter safely through the vascular system and into the delicate coronary vessels, the guiding catheter must have a soft distal tip. The soft distal tip minimizes the risk of causing trauma to a vessel, freeing plaque from a vessel wall, puncturing a vessel, or creating embolisms in the bloodstream.

One nonanalogous, nonbraided angiographic catheter comprises an inner tube of polyamide externally tapered about the distal end and jacketed by a urethane material. The urethane material is internally tapered to match the externally tapered inner tube and extends beyond the distalend of the inner tube to form a flexible tip. Although well-suited as an angiographic catheter to withstand high burst pressures of injected contrast medium, the thickness of the catheter walls severely limits the use of this catheter as a guiding catheter through which an angioplasty balloon catheter is commonly inserted. The lumen of a guiding catheter must be as large as possible with a correspondingly thin catheter wall that can be pushed and guided through tortuous coronary vessels without causing trauma thereto.

One guiding catheter includes a wire-braided Teflon material inner tube with a polyurethane jacket epoxied thereto that abruptly terminates near the distal end of the inner tube. A metal radiopaque marker and a soft polyurethane tip are positioned around the distal end of the Teflon material inner tube and abut the abrupt, step-like shoulder at the distal end of the polyurethane jacket. The polyurethane tip is thermally bonded to the polyurethane jacket. A problem with this design is that the contact surface area between the abrupt, step-like shoulder of the polyurethane jacket and the proximal end of the polyurethane tip is limited, thereby significantly increasing the likelihood that the tip will be dislodged or separated from the step-like shoulder of the jacket. The metal radiopaque marker positioned between the jacket and tip further reduces the contact surface area therebetween and increase the likelihood of jacket and tip separation.

Another problem of guiding catheters is being able to vary the durometer of the catheter along its length. Previous bonding techniques have resulted in abrupt durometer changes which affect the trackability of the catheter as well as increase the risk of trauma to surrounding vessel walls. Furthermore, previous bonding techniques have caused significant variations in the wall thickness of the guiding catheter, and thus, limit the size of balloon catheters and other devices passed therethrough.

SUMMARY OF THE INVENTION

The foregoing problems are solved and a technical advance is achieved in an illustrative guiding catheter having a main tubular portion and a soft tip with respective matching external and internal tapers for advantageously increasing the bonding area and minimizing the likelihood of separation therebetween. Furthermore, the tapers provide a gradual change in durometer between the soft tip and main tubular portion. The main tubular portion includes a layered wall between its outer surface and inner passageway surface extending longitudinally therein. The wall has a composite durometer and advantageously includes an inner material layer for lubricous insertion of other catheters therethrough and an outer material layer for increasing the compression strength and pushability of the catheter through coronary vessels. The outer layer extends the entire length of the external taper, whereas the inner layer longitudinally extends partially along the external taper to strengthen the bond between the tapers. The tubular tip comprises material having a durometer softer than the durometer of the main tubular portion for minimizing trauma to vessel walls. The proximal end of the tubular tip includes the internal taper that is bonded to the external taper of the main tubular portion.

Furthermore, the soft, tubular tip cooperates with the harder durometer main portion by readily bending in tortuous vessels when pushed therethrough. The wall of the main portion further includes a reinforcing braid for enhancing the torquability of the catheter and for minimizing kinking of the catheter when flexed. The braid also extends partially into the tapered section of the main portion to further strengthen the bond between the main portion and soft tip. The combination of the inner and outer layers with the braid therebetween also reduces the thickness of the wall to within a range of 0.006" to 0.0155" depending on the outside diameter of the catheter.

The inner layer of the wall comprises preferably polytetrafluoroethylene having an approximately 50 to 65 hardness durometer on the Shore D scale. This lubricous inner layer material also prevents the braid from extending into the passageway and presenting a rippled surface on which a passing catheter may undesirably engage. The outer layer of the wall preferably comprises polyether block amide including by weight 10 to 30 percent radiopaque bismuth, which is softer in durometer than the composite durometer of the catheter as well as that of the inner wall material. The soft, tubular tip comprises another polyether block amide that is softer in durometer than the outer wall material and advantageously includes by weight 35 to 65 percent tungsten for increasing the radiopacity of the soft tip.

In particular, the illustrative 8 French guiding catheter has a uniform outside diameter of approximately 0.103", a uniform inside diameter of approximately 0.082", and a wall thickness of nominally 0.0105" for inserting the largest possible angioplasty balloon catheter therethrough. The tubular tip has an internal taper extending longitudinally in a range of 2 to 3 mm with the inner layer of the main portion extending partially therealong in a range of 1 to 2 mm.

The foregoing problems are also solved and another technical advance is achieved in an illustrative guiding catheter having a main tubular portion and a soft tubular tip with cooperating bonding surfaces for advantageously increasing the bonding area and minimizing the likelihood of separation therebetween. Each of the cooperating bonding surfaces has a proximal tapered portion and a distal longitudinal portion extending from the distal end of the main tubular portion. Advantageously, braiding material included in the main tubular portion and positioned around the tube extends only into the tapered portion of the bonding surfaces. The braiding material is removed from the longitudinal portion of the main tubular portion bonding surface to provide spiral grooves therein to enhance the strength and integrity of a heat bond formed at the cooperating bonding surfaces.

To increase the area of the bonding surfaces as well as the change in durometer longitudinally along the heat bond, the tapered portions of the bonding surfaces are approximately four times greater in longitudinal length than the distal longitudinal portions of the bonding surfaces.

To advantageously increase the durometer of the catheter along its entire length, the main tubular portion of the catheter includes distal and proximal outer surface materials having a heat shrink bond therebetween. These outer surface materials are also heat shrink bonded to an inner tube through braiding material. The distal outer surface material has a durometer lower than that of the proximal outer surface material. As a result, longer lengths of guiding catheters can be formed with increased pushability. Furthermore, a relatively soft material tubular tip is bonded to the main tubular portion with first and second cooperating bonding surfaces having a heat bond therebetween.

BRIEF DESCRIPTION OF THE DRAWING

FIG. 1 depicts a partially cross-sectioned view of an illustrative soft tip guiding catheter of the present invention for atraumatic insertion through coronary vessels and introduction of an angioplasty balloon catheter therethrough;

FIG. 2 depicts a partially cross-sectioned view of the wall of the guiding catheter of FIG. 1;

FIG. 3 depicts an enlarged partially sectioned view of an alternative embodiment of the bonding between the tubular tip and the main tubular portion of the guiding catheter of FIG. 1; and FIG. 4 depicts heat shrink bonding of distal and proximal segments of the main tubular portion of the guiding catheter of FIG. 1.

DETAILED DESCRIPTION

FIG. 1 depicts a partially cross-sectioned view of illustrative soft tip guiding catheter 10 having main tubular portion 11 and soft tubular tip 12 with thermal bond 15 interconnecting mated external and internal tapers 13 and 14, respectively. The inner and outer diameters of the main portion are uniform and match those of the soft tip for inserting the largest possible angioplasty balloon catheter therethrough and providing a uniform outer catheter surface for ready insertion through a coronary vessel. Multilayered catheter wall 21 of the main portion includes lubricous inner layer 25 and compression resistant outer layer 27. Reinforcing braid 26 is positioned around inner layer 25 for making the thin catheter wall torquable and minimizing kinking when directing the catheter through tortuous coronary vessels. The composite durometer such as 48 on the Shore D scale of the main portion is hard so as to advance the catheter to the coronary vessels. The soft durometer tip minimizes vessel wall trauma. The internal and external tapers increase the strength of thermal bond 15 to prevent separation from the main portion and also provide a gradual change in the durometer of the catheter between the main portion and tubular tip.

The soft tip includes proximal end 22 with internal taper 14, distal end 23, and passageway 24 extending longitudinally therethrough. Wall 33 of the tubular tip extends between inner passageway surface 31 and outer surface 32. The soft tip preferably comprises a soft durometer polyether block amide material such as nylon with a durometer of approximately 75 on the Shore A scale and having by weight in a range of 35 to 65 percent tungsten. The tungsten significantly increases the radiopacity of the soft tip. Preferably, soft tip 12 is a 2 cm length of 7.8 French nylon material tube including by weight 50 percent nylon and 50 percent tungsten. Internal taper 14 extends longitudinally approximately 2 to 3 mm about distal end 23. Distal end 23 is rounded inside and out for presenting an atraumatic end surface. Thermal bond 15 between external and internal tapers 13 and 14 is formed using any of a number of well-known techniques.

The main portion includes proximal end 16, distal end 17 with external taper 13, and passageway 18 extending longitudinally therethrough communicating with passageway 24 of the soft tip. Wall 21 extends between inner passageway surface 19 and outer surface 20. Outer surface 20 and inner surface 19 of the main portion have respective diameters approximating the respective diameters of outer surface 32 and inner surface 31 of the soft tip. As a result, the guiding catheter has a smooth, uniform outer surface for ready and atraumatic insertion through coronary vessels and a smooth, uniform inner passageway surface for introducing the largest possible angioplasty balloon catheter therethrough. Guiding catheter 10 preferably has a uniform 8 French outside diameter of approximately 0.103", a uniform inside diameter of approximately 0.082", and a wall nominally 0.0105" in thickness. Well-known connector cap 28 and winged flange 29 are fixedly attached about proximal end 16 of the main portion by a commercially available, medical grade adhesive 30, such as Loctite No. 401, for providing a handle to manipulate the catheter.

FIG. 2 depicts a partially cross-sectioned view of main portion wall 21 and soft tip wall 33. Soft tip wall comprises 50 percent polyether block amide for atraumatic insertion and 50 percent tungsten, shown as particles 34, for radiopacity.

Main portion wall 31 includes inner layer 25, reinforcing braid 26, and outer layer 27. Inner layer 25 comprises a lubricous material such as polytetrafluoroethylene having an approximately 50 to 65 durometer on the Shore D scale for providing a slick inner passageway surface. To increase the strength of thermal bond 15, the inner layer longitudinally extends partially along external taper 13, which is approximately 2 to 3 mm in length, for approximately 1 to 2 mm. In the preferred embodiment, inner layer 25 comprises a 130 cm length of 6.7 French polytetrafluoroethylene tube.

The main portion wall further includes reinforcing braid 26 of, for example, stainless steel wire, for enhancing the torquability and kink resistance of the catheter. The braid also longitudinally extends partially along the external taper for further strengthening the bond thereat. In the preferred embodiment, braid 26 is 175 cm long with an outside diameter of 0.078" and having a pic of 50 formed of 0.0026" and 0.0030" diameter Series 304 stainless steel wire. Inner layer 25 prevents the braid from rippling inner passageway surface 19 and undesirably engaging another catheter being passed therethrough.

The main portion wall further comprises outer layer 27 longitudinally extending the entire length of the external taper. The outer layer preferably also comprises a polyether block amide such as nylon for increasing the compression strength and pushability of the catheter and includes by weight in a range of 10 to 30 percent bismuth, shown by particles 35, for radiopacity. The polyether block amide material of the outer layer is softer in durometer than the composite durometer of the catheter as well as that of the inner layer. In particular, outer layer 27 is a 130 cm length of 9 French nylon material tube comprising by weight approximately 90 percent nylon with a durometer of approximately 60.7 on the Shore D scale and 10 percent bismuth. The combination of the inner and outer layers with the braid positioned therebetween comprises a wall thickness in a range of 0.006" to 0.0155" depending on the outside diameter of the catheter and has a composite durometer of approximately 48 on the Shore D scale. Multilayered wall 21 is thermally bonded using any of a number of well-known techniques.

FIGS. 3 and 4 depict enlarged partially sectioned views of tubular tip portion 12 and the distal and proximal segments of main tubular portion 11 of an alternative embodiment of soft tip guiding catheter 10 of FIG. 1, respectively. FIG. 3 depicts an alternative embodiment of bonding tubular tip 12 to main tubular portion 11. Tubular tip 12 of relatively soft polyether block amide material 36 has a longitudinal passageway 24 extending therethrough which communicates with passageway 18 of main tubular portion 11. In this embodiment, relatively soft material 36 comprises a polyether block amide such as nylon with a durometer of approximately 25 on the Shore D scale and includes a radiopaque material 34, preferably, of tungsten by weight in a range of 76 to 95 percent tungsten. Preferably, soft tubular tip 12 is approximately 7 mm in length with an outside diameter of 0.107" and an inside diameter of 0.086" and includes by weight 20 percent nylon and 80 percent tungsten. The tubular tip includes a first cooperating bonding surface 37 proximate proximal end 22 of the tip, which is heat bonded to second cooperating bonding surface 38 proximate distal end 17 of main tubular portion 11. First bonding surface 37 includes a proximal tapered portion 39 and a distal longitudinal portion 41, which extends proximally from distal end 17 of the main tubular portion or distally from proximal end 22 of the soft tubular tip. A thermal or heat bond 15 joins cooperating bonding surfaces 37 and 38.

Cooperating bonding surface 38 of the main tubular portion is prepared by centerless grinding distal outer surface material 27 and wire braid 26 about distal end 17 of the main tubular portion. The tapered portion extends longitudinally for approximately 4 mm to form proximal tapered portion 40. Distal longitudinal portion 42 of bonding surface 38 extends longitudinally for approximately 1 mm and does not contain any wire braid therein. The wire braid has been removed from this distal longitudinal portion and left a number of spiral grooves in the distal outer surface material. This substantially improves the bonding between the outer surface and tip materials. In addition, the proximal tapered portion of the distal outer surface material and the soft tip material provides a gradual change in durometer, which substantially increases the trackability of the guiding catheter and reduces trauma to surrounding vessel walls. Although the longitudinal length of the tapered portion of the bending surface has been indicated as being approximately four times the longitudinal length of the distal longitudinal portion of the bonding surface, the tapered portion can range from one to six times the length of the longitudinal portion. Reducing the tapered portion to less than one times the length of the longitudinal portion causes an abrupt change in durometer which significantly reduces the trackability of the catheter as well as increasing the likelihood of trauma to surrounding vessel walls.

Cooperating bonding surface 37 of the tubular tip is formed by centerless grinding the outer surface of the tubular tip material to form an external taper and then flaring the externally tapered proximal end of the tip over second bonding surface 38 of the main tubular portion. To form heat bond 15, a mandril (not shown) is inserted through passageways 18 and 24 of the main tubular portion and tubular tip and then inserted into a forming die to which radiofrequency energy is commonly applied for melting distal outer surface material 27 and soft material 36 together to form the heat bond.

FIG. 3 also depicts distal segment 44 of main tubular portion 11. This segment of main tubular portion 11 includes outer distal surface material 27 heat shrink bonded to polytetrafluoroethylene tube 25 through previously described wire braid 26. To improve the bonding therebetween, the outer surface 43 of the inner tube is roughened. Distal outer surface material 27 comprises a polyether block amide having a durometer of approximately 59 on the Shore D hardness scale. The distal outer surface material also includes a radiopaque material 35, preferably, of bismuth in a range of 10 to 30 percent by weight. To further enhance the bond between distal segment 44 of the main tubular portion and tubular tip 12, wire braid 26 extends up to and is included in tapered portion 40 of bonding surface 38. Furthermore, the increased durometer of the distal segment of the main tubular portion provides increased pushability of the catheter while minimizing trauma to vessel walls.

FIG. 4 depicts the bonding of distal segment 44 to proximal segment 46 of main tubular portion 11 of the guiding catheter. Proximal segment 46 of the main tubular portion includes proximal outer surface material 45 of polyether block amide having a higher durometer than that of distal outer surface material 27. Proximal outer surface material 45 has a durometer of approximately 75 on the Shore D hardness scale. Proximal and distal outer surface materials 45 and 27 are bonded together at heat shrink bond 47. Heat shrink bond 47 is formed by centerless grinding distal end 50 of proximal outer surface material 45 into ground taper surface 52 and proximal end 49 of distal outer surface material 27. The proximal end of the distal outer surface material is then flared and inserted over ground taper surface 52 to form cooperating ground taper surface 51.

Main tubular portion 11 is formed by positioning wire braid 26 over a 130 cm length of polytetrafluoroethylene tube 25. Proximal outer surface material 45 and distal outer surface material 27 are then positioned as previously described over the wire braid and tube. A heat shrink tube is then positioned over the entire catheter tube and then heated to heat shrink outer surface materials 27 and 45 to the outer surface of the tube through wire braid 26. A very uniform thickness catheter wall is thus formed while providing a gradual change in durometer from distal segment 44 to proximal segment 46 of the main tubular portion. Proximal segment 46 of the main tubular portion of the catheter has a higher durometer than distal segment 44 to further increase the pushability of the catheter. Additional increasing durometer segments of the catheter can be formed as previously described with even higher durometer outer surface materials. As a result, a soft tip guiding catheter is formed with increasing segments of durometer hardness from the soft tip to the proximal end of the catheter.

Heat shrink bond 47 can extend longitudinally for up to approximately 2" in length. Cooperating ground taper bonding surfaces 51 and 52 are limited only by the centerless grinding operation, which will not distort the uniformity of the tapers.

It is to be understood that the above-described soft tip guiding catheter is merely an illustrative embodiment of the principles of this invention and that other embodiments may be devised by those skilled in the art without departing from the spirit and scope of this invention. It is contemplated that various other materials of comparable durometers may be utilized for the inner or outer layers, reinforcing braid, or soft tip. In summary, the combination of material layers in the main portion of the guiding catheter provides a thin wall with pushability, torquability, and kink resistance. The soft tip thermally bonded to the main portion by respective tapers presents a soft, atraumatic surface to delicate coronary vessels.

What is claimed is:

1. A soft tip guiding catheter (10) comprising:
a main tubular portion (11) including a distal outer surface material (27), an inner tube (25) lining a passageway (18) of said main tubular portion and extending proximally from a distal end (17) thereof, and a braiding material (26) positioned around said inner tube;
a tubular tip (12) of relatively soft material (36) forming a longitudinal passageway (24) with said passageway of said main tubular portion; and
first (37) and second (38) cooperating bonding surfaces, said first bonding surface on said main tubular portion and said second bonding surface on said tubular tip, said first and said second cooperating bonding surfaces each having a longitudinal portion (42) essentially parallel to said passageway (18) and a tapered portion (41), wherein said longitudinal portion of each bonding surface is distal to said tapered portion, wherein said first and second bonding surfaces form a bond at the interface of said surfaces, and wherein said braiding material further extends along the tapered portions of said first and said second cooperating bonding surfaces.

2. The catheter of claim 1 wherein said distal outer surface material (27) has a first durometer extending along a distal segment (44) of said main tubular portion and wherein said main tubular portion comprises a proximal outer surface material (45) having a second durometer higher than said first durometer and extending along a proximal segment (46) of said main tubular portion.

3. The catheter of claim 2 wherein said distal and said proximal outer surface materials include a heat shrink bond (47) therebetween at a proximal end (49) and a distal end (50) thereof, respectively.

4. The catheter of claim 3 wherein said distal and said proximal outer surface materials include first (51) and second (52) cooperating ground taper bonding surfaces at said proximal and said distal ends, respectively.

5. The catheter of claim 1 wherein said inner tube is of polytetrafluoroethylene.

6. The catheter of claim 5 wherein said inner tube has a rough outer surface (43).

7. The catheter of claim 1 wherein said distal outer surface material is of polyether block amide with a first durometer and wherein said soft material of said tubular tip is of polyether block amide and has a second durometer lower than said first durometer of said distal outer surface material.

8. The catheter of claim 7 wherein said distal outer surface material includes a radiopaque material (35) dispersed therein and in a range of 10 to 30 percent and wherein said soft material of said tubular tip includes a radiopaque material (34) in a range of 76 to 95 percent.

9. The catheter of claim 1 wherein the tapered portions of said first and second cooperating bonding surfaces are approximately four times greater in longitudinal length than the distal longitudinal portions of said first and said second cooperating bonding surfaces.

10. A soft tip guiding catheter (10) comprising:
a main tubular portion (11) including a distal (27) and a proximal (45) outer surface material, an inner tube (25) lining a passageway (18) of said main tubular portion and extending proximally from a distal end (17) thereof, and a braiding material (26) positioned around said inner tube, said distal and said proximal outer surface materials having a heat shrink bond (47) therebetween and with said inner tube through said braiding material;
a tubular tip (12) of relatively soft material (36) forming a longitudinal passageway (24) with said main tubular portion; and
first (39) and second (40) cooperating bonding surfaces, said first bonding surface on said main tubular portion and said second bonding surface on said tubular tip, wherein said first and said second cooperating bonding surfaces each have a longitudinal portion and a tapered portion, wherein said longitudinal portion of each bonding surface is distal with respect to said tapered portion, and wherein said first and second bonding surfaces form a heat bond (15) therebetween.

11. The catheter of claim 10 wherein said first and said second cooperating bonding surfaces each has a distal longitudinal portion (42) extending proximally from said distal end of said main tubular portion and a proximal tapered portion (41) positioned proximal of said distal longitudinal portion, said braiding material further extending along the tapered portions of said first and said second cooperating bonding surfaces.

12. The catheter of claim 11 wherein the tapered portions of said first and second cooperating bonding surfaces are approximately four times greater in length than the distal longitudinal portions of said first and said second cooperating bonding surfaces.

13. The catheter of claim 10 wherein said distal outer surface material has a first durometer lower than a second durometer of said proximal outer surface material.

14. The catheter of claim 10 wherein a proximal end (49) of said distal outer surface material and a distal end (50) of said proximal outer surface material have first (51) and second (52) cooperating ground taper bonding surfaces, respectively.

15. The catheter of claim 10 wherein said distal outer surface material includes a radiopaque material (35) of bismuth in a range of 10 to 30 percent.

16. The catheter of claim 10 wherein said soft material of said tubular tip includes a radiopaque material (34) of tungsten in a range of 76 to 95 percent.

17. The catheter of claim 10 wherein said inner tube is of polytetrafluoroethylene.

18. The catheter of claim 10 wherein said distal and said proximal outer surface materials and said soft material of said tubular tip is of polyether block amide.

19. A soft tip guiding catheter (10) comprising:
a main tubular portion (11) and including a distal (27) and a proximal (45) outer surface material, an inner tube (25) with a rough outer surface (43) lining a passageway (18) of said main tubular portion and extending proximally from a distal end (17) thereof, and a braiding material (26) positioned around said tube, said distal and said proximal outer surface materials having first (51) and second (52) cooperating ground taper surfaces at a proximal end (49) of said distal outer surface material and a distal end (50) of said proximal outer surface material, respectively, said first and said second cooperating ground taper surfaces having a heat shrink bond (47) therebetween, said distal and said proximal outer surface materials being heat shrink bonded to said rough outer surface of said inner tube through said braiding material, said distal and said proximal outer surface materials comprising polyether block amide, at least one of said distal and said proximal outer surface materials including a radiopaque material (35) of bismuth in a range of 10 to 30 percent;

a tubular tip (12) of relatively soft polyether block amide material (36) including a radiopaque material (34) of tungsten in a range of 76 to 95 percent and forming a longitudinal passageway (24) with said passageway of said main tubular portion, said relatively soft polyether block amide material having a durometer less than the durometer of said distal and said proximal outer surface materials, said proximal outer surface material having a durometer greater than the durometer of said distal outer surface material; and first (37) and second (38) cooperating bonding surfaces, said first bonding surface on said main tubular portion and said second bonding surface on said tubular tip, said first and said second cooperating bonding surfaces having a heat bond (15) therebetween, said first and said second cooperating bonding surfaces each having a longitudinal portion (42) and a tapered portion (41), wherein said longitudinal portion is distal to said tapered portion and is essentially parallel to said passageway (18), and wherein said braiding material further extends along the tapered portions of said first and said second cooperating bonding surfaces.

\* \* \* \* \*